United States Patent
Gygax et al.

[11] Patent Number: 6,147,049
[45] Date of Patent: Nov. 14, 2000

[54] TETRA-HYDRONAPHTHALENES

[75] Inventors: Peter Gygax, Fällanden; Hans-Ulrich Gonzenbach, Genève, both of Switzerland

[73] Assignee: Givaudan Roure (International) SA, Vernier-Geneve, Switzerland

[21] Appl. No.: 09/460,248

[22] Filed: Dec. 13, 1999

[51] Int. Cl.$^7$ ........................................................ A61K 7/46
[52] U.S. Cl. ............................ 512/2; 568/309; 568/323; 568/328; 570/190
[58] Field of Search .................. 512/2; 568/328, 568/309, 323; 570/190

[56] References Cited

U.S. PATENT DOCUMENTS 2,800,511 7/1957 Carpenter et al.

FOREIGN PATENT DOCUMENTS 1359195 7/1964 France.

OTHER PUBLICATIONS

Narvaez et al, Chem. Abstr., vol. 104, No.213002e, 1986.
Bersuker et al, Chem. Abstr., vol. 115, No. 89815h, 1991.
Chastrette et al, Chem. Abstr., vol. 122, No. 77401b, 1995.
Chastrette et al, Chem. Abstr., vol. 123, No. 281926b, 1995.
Chastrette et al, Chem. Abstr., vol. 129, No. 347, 126y, 1998.
Berner,E., *Acta Chemica Scand.*, vol. B36(10):729–31, (1982).
Sengul, M.E., et al., *J. Chem. Soc. Perkin Trans. I*, 2071–2077, (1997).
Dawson, M.I., et al.,*J. Med. Chem*, 32(7):1504–1517 (1989).

*Primary Examiner*—James H. Reamer
*Attorney, Agent, or Firm*—Mark E. Waddell; Stephen M. Haracz; Bryan Cave LLP

[57] ABSTRACT

The present invention provides compounds of formula I:

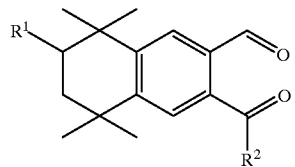

wherein $R^1$ is hydrogen or methyl and $R^2$ is alkyl. These compounds are useful as fixatives in fragrance compositions. Processes of making such compounds are also provided.

18 Claims, No Drawings

TETRA-HYDRONAPHTHALENES

FIELD OF THE INVENTION

The present invention relates to new tetra-hydronaphthalenes, processes for preparing, and compositions containing these compounds.

BACKGROUND OF THE INVENTION

Fragrance compositions consist of a number of components having different volatility. During storage and application of such fragrance compositions, the more volatile components evaporate faster, altering the quality thereof. To maintain the fragrant quality of such compositions over a longer period of time, measures have to be taken to prevent early evaporation of the more volatile components. Generally, so called "fixatives" are added to the compositions. Such fixative compounds form loose complexes with the more volatile components of the fragrance composition, thus reducing the volatility thereof. The fixative compounds may either be odorless or have an odor which contributes to the scent of the fragrance composition. For the perfumer, it is easier to use odorless fixatives because they do not impart an additional odor to the fragrance composition, and therefore allow a dosage over a wider range without altering much of the fragrance quality of the composition. Further odorless fixatives may be used in a wide range of different fragrance compositions.

SUMMARY OF THE INVENTION

One embodiment of the present invention is a compound of formula I:

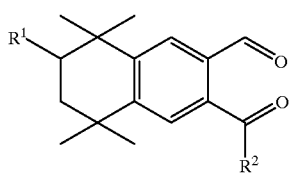

wherein $R^1$ is hydrogen or methyl, and $R^2$ is alkyl. Such a compound is odorless and is useful as a fixative.

As the skilled person knows, o-diacylarenes can not be prepared by double Friedel-Crafts-acylation of the parent arene due to the strong de-activation of the first introduced acyl group.

In principle, o-acylbenzaldehydes may be prepared from o-acylcinnamic acids, however, the oxidation steps inefficiently use transition metals (E. Berner, Acta Chemica Scand. Ser. B, 729 (1982)). An alternative synthesis would use an acetylheptatriene, which is not easily available and would require a low yield air-oxidation in the last step, a procedure which is potentially dangerous (M. Senguel, J. Chem. Soc. Perkin Trans. I, 2071 (1997)).

Therefore, one embodiment of the invention is a new process that avoids the drawbacks of the known processes for the preparation of compounds of formula I:

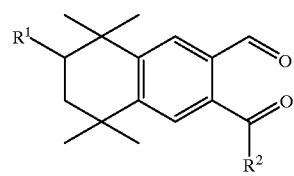

wherein $R^1$ is hydrogen or methyl and $R^2$ is alkyl is also provided. This process includes (a) reacting a compound of formula II:

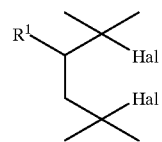

with a compound of formula III:

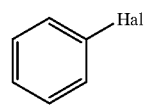

wherein Hal is halogen; (b) acylating a tetrahydronaphthalene of formula IV:

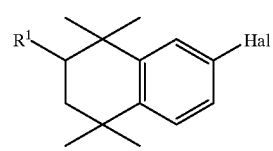

produced by the reaction in (a) to form a compound of formula V:

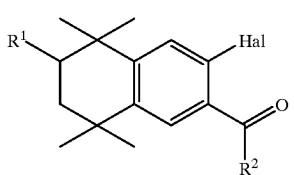

(c) reacting a compound of formula V with an alcohol or glycol to form a ketal of formula VI:

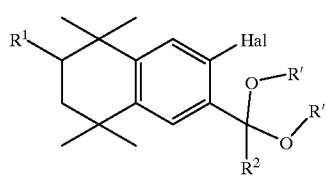

wherein R' is an alkyl residue or R'—R' is a divalent alkyl residue that forms a dioxolane ring; and (d) reacting a compound of formula VI with magnesium and a formamide of formula VIII:

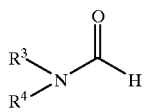

VIII to form a compound of formula I, wherein $R^3$ and $R^4$ are two organic residues or together form a ring.

A fragrance composition is also provided that includes a fragrance and a fixative, wherein the fixative is a compound of formula I:

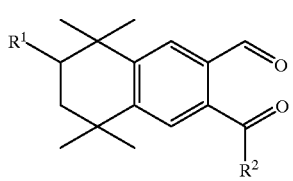

I wherein $R^1$ is hydrogen or methyl, and $R^2$ is alkyl.

In this embodiment, highly volatile alcohols may be added to the fragrance composition. As used herein, the phrase "highly volatile alcohols" is intended to mean any alcohol-function-containing compound useful in fragrance compositions and which tends to quickly evaporate upon exposure to ambient conditions.

DETAILED DESCRIPTION OF THE INVENTION

In the present invention, it has been found that the following five-step method using readily available starting materials provides the desired compound of formula I with a good yield:

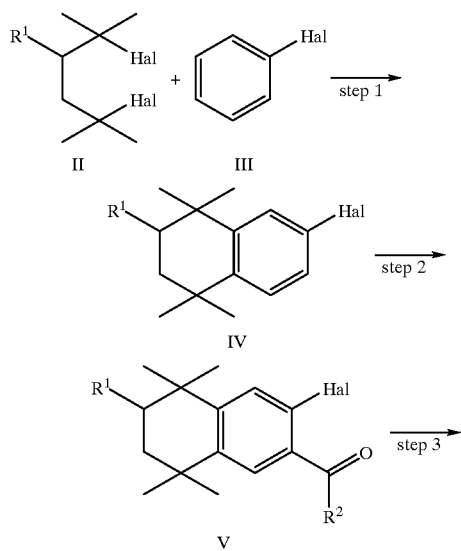

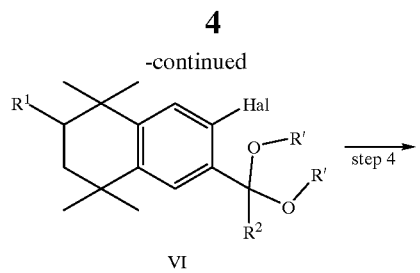

VI

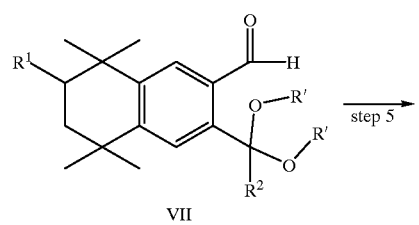

VII

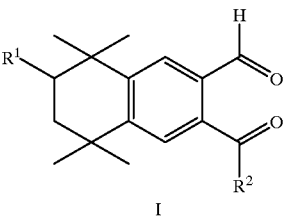

I

In the formulae, $R^1$ is either hydrogen or methyl, Hal is a halogen, preferably Br or Cl, R' is alkyl, preferably a lower alkyl, such as for example methyl, or R'—R' is a divalent alkyl residue that forms a dioxolane ring, and $R^2$ is alkyl, preferably $C_{1-12}$-alkyl, such as for example $C_{1-4}$-alkyl.

In step 1 above, a halobenzene, preferably bromo- or chlorobenzene, is condensed with a 2,5-dihalo-2,5-dimethylhexane. The condensation is run in the presence of a small amount of a Lewis-acid catalyst, such as for example aluminum chloride, ferric chloride, and bismuth chloride. However, other catalysts capable of carrying out alkylations of arenes may also be used in the present invention. The substituted tetraline derivatives (IV) obtained in this way may be isolated and purified.

The introduction of the acyl group (step 2) is accomplished by the reaction of the tetraline (IV) with an activated acid derivative in the presence of a Friedel-Crafts-acylation-catalyst. Acid chlorides or acid anhydrides for example, may be used as activated acid derivatives. The catalysts again may be Lewis acids as set forth above.

To make the procedure more economic, steps 1 and 2 may also be carried out without isolation of the compound of formula IV. To avoid undesired side reactions, the amount of catalyst used in step 1 must be kept small. Thus, just before the acylation-step (2), more catalyst is added. As the acyl group of V is not compatible with the Grignard reaction (step 4), it is protected as a ketal. This may be accomplished by reacting a compound of formula V with alcohols or orthoesters or by transketalization. This reaction is usually catalyzed by an acid, such as a Lewis or a protic acid. Examples of acid catalysts useful in the present invention include sulfonic acids, sulfuric acid, clays etc. Instead of monohydric alcohols, diols such as for example ethylene glycol may also be used.

Compounds of formula VII are then transformed into an organometallic species, such as a lithium or a magnesium derivative, by treatment of a compound of formula VI with magnesium, lithium or a lithiumalkyl, such as for example butyllithium. The use of magnesium in this reaction is preferred for economical reasons. The formyl group is preferably introduced by reaction of the organometallic intermediate with formic acid or a derivative thereof, most easily and economically by means of a formamide such as dimethylformamide, N-alkyl-formanilide or formylmorpholine. Although it is possible to isolate the formyl-ketals (VII), it is more practical and more economic to hydrolyze them without any workup by treating the reaction mixture with water at an acidic pH-value.

As set forth above, the compounds of formula I are odorless and show excellent fixative qualities in different fragrance compositions resulting in improved linear behavior, i.e., a high stability of the fragrance quality. These compounds may be used for a wide range of fragrance compositions.

The following examples are set forth to illustrate the synthesis of the compounds of the present invention and their use in various compositions. These examples are illustrative only and are not intended to limit the scope of the invention in any way.

EXAMPLES

Example 1
1,1,4,4-Tetramethyl-6-acetyl-7-formyl-1,2,3,4-tetrahydronaphthalene 219.6 g 2,5-Dichloro-2,2,5,5-tetramethyl-hexane dissolved in 480 ml dichloroethane were added over 1 hour to 8.4 g aluminum chloride suspended in 217 g bromobenzene at −10° C. After stirring for 20 minutes, 204 g aluminum chloride were added, followed by 127 g acetylchloride. The slurry was then stirred at 0° C. for 4 hours and then at room temperature for 12 hours. The dark mass that was formed was then poured into 2l of ice-water. The organic phase was washed twice with water, dried, and evaporated to dryness. Distillation of the residue provided 240.6 g 1,1,4,4-tetramethyl-6-acetyl-7-bromo-1,2,3,4-tetrahydronaphthalene, $bp_{0.08\ Torr}$: 148–152° C.

NMR (CDCl$_3$): 7,5(s, 1H), 7,45(s, 1H), 2,63(s, 3H), 1,67(s, 4H), 1,27(s, 12H)

240.6 g 1,1,4,4-Tetramethyl-6-acetyl-7-bromo-1,2,3,4-tetrahydronaphthalene, 96.7 g ethyleneglycol, 11 g Amberlyst 15 and 120 ml hexane were refluxed over night in a flask equipped with a Dean-Stark water trap. Afterwards, a further 50 g of ethyleneglycol were added and refluxing was continued for another 12 hours. The reaction mixture was then diluted with ether and filtered from the catalyst. The solution was then washed with 1l water containing 2 g sodium carbonate and then twice with water, dried, and evaporated to dryness. Crystallization of the residue from hexane provided 137 g 1,1,4,4-Tetramethyl-6-acetyl-7-bromo-1,2,3,4-tetrahydronaphthalene-ethyleneketal.

NMR (CDCl$_3$): 7,55(s, 1H), 7,47(s, 1H), 3,97–4,15(m, 2H), 3,69–3,85(m, 2H), 1,82(s, 3H), 1,65(s, 4H), 1,25(s, 12H)

To 1.02 g magnesium-turnings suspended in 6 ml tetrahydrofurane, 310 mg ethylbromide were slowly added. When the Grignard reaction had started, 10.59 g 1,1,4,4-Tetramethyl-6-acetyl-7-bromo-1,2,3,4-tetrahydronaphthaleneethyleneketal dissolved in tetrahydrofurane were added at reflux temperature over a period of several minutes. After refluxing for 2 additional hours, 4.5 g N,N-dimethylformamide were added at 0° C. and the mixture was stirred at this temperature for 3 hours. The reaction mixture was then refluxed for 3 hours. The reaction mixture was then poured into 2N HCl and extracted with ether. The organic phase was washed with water, evaporated to dryness, and refluxed for 2 hours with 60 ml 2N HCl/ml water. After the usual workup, 8.38 g 1,1,4,4-Tetramethyl-6-acetyl-7-formyl-1,2,3,4-tetrahydronaphthalene were obtained with a melting point of 116° C.: (hexane).

NMR(CDCl$_3$): 7,84(s, 1H), 7,63(s, +H), 2,63(s, 1H), 1,71(s, 4H), 1,33(s, 12H)

Example 2
1,1,2,4,4-Pentamethyl-6-acetyl-7-formyl-1,2,3,4-tetrahydronaphthalene This compound was prepared according to Example 1 by acetylation of 1,1,2,4,4-Pentamethyl-7-bromo-1,2,3,4-tetrahydonaphtalene, ketalisation with ethyleneglycol, and Grignard-reaction with N-formylmorpholine.

NMR(CDCl$_3$): 10,2(s, 1H), 7,9(s, 1H), 7,62(s, 1H), 2,64 (s, 3H), 1,8–2,0(m, 1H), 1,68(t, 2H), 1,45 (dxd, 1H), 1,38(s, 3H), 1,36(s, 3H), 1,10(s, 3H), 1,02(d, 3H)

Example 3

Use of 1,1,4,4-Tetramethyl-6-acetyl-7-formyl-1,2,3,4-tetrahydronaphthalene as fixative A muguet-type fragrance composition containing the following elements was prepared.

| Element | Parts |
| --- | --- |
| Indole | 5 |
| Benzylacetate | 7 |
| cis-3-Hexenyl-acetate (10%) | 7 |
| Rose oxide (1%) | 5 |
| Hedione | 10 |
| Lilial | 20 |
| cis-3-Hexenyl-benzoate | 15 |
| Nerol | 15 |
| cis-3-Hexenol | 10 |
| Cinnamyl alcohol | 30 |
| Citronellyl acetate | 30 |
| Rhodinol | 30 |
| Phenylethanol | 20 |
| Citronellol | 75 |
| Benzyl benzoate | 70 |
| Geraniol | 70 |
| Geranyl acetate | 80 |
| Nerolidol | 80 |
| Farnesol | 120 |
| Benzylic alcohol | 150 |
| Hydroxycitronellal | 50 |
| Dipropylene glycol | 101 |

Addition of 1,1,4,4-Pentamethyl-6-acetyl-7-formyl- 1,2,3,4-tetrahydronaphthalene to the composition resulted in improved linear behavior of the fragrance composition (i.e., the scent of the fragrance composition was stable over a longer period) compared to a composition not containing the fixative.

Example 4
Use of 1,1,2,4,4-Pentamethyl-6-acetyl-7-formyl-1,2,3,4-tetrahydronaphthalene as fixative Addition of 1,1,2,4,4-Pentamethyl-6-acetyl-7-formyl-1,2,3,4-tetrahydronaphthalene to a muguet-type fragrance composition according to example 3 resulted in improved linear behavior of the fragrance composition(i.e., the scent of the fragrance composition was stable over a longer period) compared to a composition not containing the fixative.

The invention being thus described, it will be obvious that the same may be varied in many ways. Such variations are not to be regarded as a departure from the spirit and scope

We claim:

1. A compound of formula I:

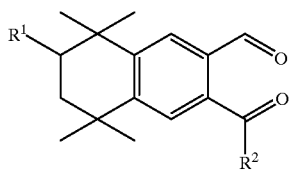

wherein $R^1$ is hydrogen or methyl and $R^2$ is alkyl.

2. A compound according to claim 1 wherein $R^2$ is a $C_{1-12}$-alkyl.

3. A compound according to claim 2 wherein $R^2$ is a $C_{1-4}$-alkyl.

4. A compound according to claim 1 wherein the compound is 1,1,4,4-tetramethyl-6-acetyl-7-formyl-1,2,3,4-tetrahydronaphthalene.

5. A compound according to claim 1 wherein the compound is 1,1,2,4,4-pentamethyl-6-acetyl-7-formyl-1,2,3,4-tetrahydronaphthalene.

6. A process for preparing a compound of formula I:

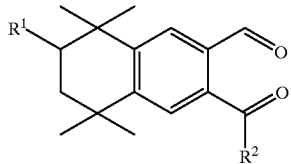

wherein $R^1$ is hydrogen or methyl and $R^2$ is alkyl comprising:

(a) reacting a compound of formula II:

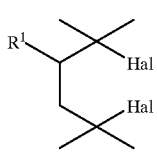

with a compound of formula III:

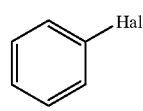

wherein Hal is halogen;

(b) acylating a tetrahydronaphthalene of formula IV:

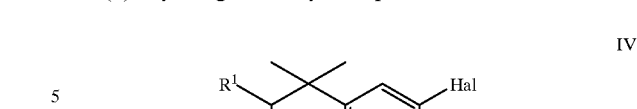

produced by the reaction in (a) to form a compound of formula V:

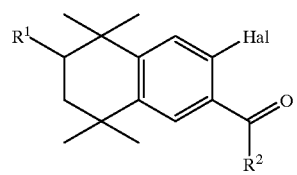

(c) reacting the compound of formula V with an alcohol or a glycol to form a ketal of formula VI:

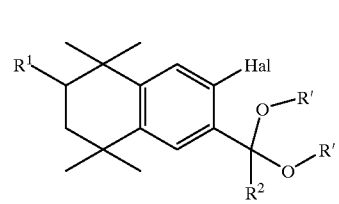

wherein R' is an alkyl residue or R'—R' is a divalent alkyl residue that forms a dioxolane ring; and (d) reacting a compound of formula VI with magnesium and a formamide of formula VIII:

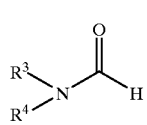

to form a compound of formula I, wherein $R^3$ and $R^4$ are two organic residues or together form a ring.

7. A process according to claim 6 wherein Hal is selected from the group consisting of Cl and Br.

8. A process according to claim 6 wherein compounds IV and/or VII are not recovered.

9. A process according to claim 7 wherein compounds IV and/or VII are not recovered.

10. A process according to claim 6 wherein the compound of formula VIII is selected from the group consisting of dimethylformamide, N-formylmorpholine, and N-methylformanilide.

11. A process according to claim 7 wherein the compound of formula VIII is selected from the group consisting of dimethylformamide, N-formylmorpholine, and N-methylformanilide.

12. A process according to claim 8 wherein the compound of formula VIII is selected from the group consisting of dimethylformamide, N-formylmorpholine, and N-methylformanilide.

13. A fragrance composition comprising a fragrance and a fixative, wherein the fixative is a compound of formula I:

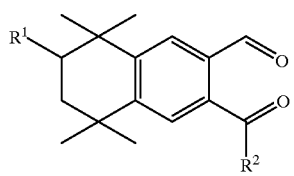

wherein R¹ is hydrogen or methyl and R² is alkyl.

14. A fragrance composition according to claim 13 wherein the fixative is 1,1,4,4-tetramethyl-6-acetyl-7-formyl-1,2,3,4-tetrahydronaphthalene.

15. A fragrance composition according to claim 13 wherein the fixative is 1,1,2,4,4-pentamethyl-6-acetyl-7-formyl- 1,2,3,4-tetrahydronaphthalene.

16. A fragrance composition according to claim 13 further comprising a highly volatile alcohol.

17. A fragrance composition according to claim 14 further comprising a highly volatile alcohol.

18. A fragrance composition according to claim 15 further comprising a highly volatile alcohol.

* * * * *

UNITED STATES PATENT AND TRADEMARK OFFICE
CERTIFICATE OF CORRECTION

PATENT NO. : 6,147,049  
DATED : November 14, 2000  
INVENTOR(S) : Peter Gygax, et al.

It is certified that error appears in the above-identified patent and that said Letters Patent is hereby corrected as shown below:

<u>Title page,</u>  
Under item [30] FOREIGN APPLICATION PRIORITY DATA, please add  
-- December 15, 1998 [EP] Europe 98811229.8 --

Signed and Sealed this

Twenty-third Day of October, 2001

Attest:

NICHOLAS P. GODICI  
*Attesting Officer*     *Acting Director of the United States Patent and Trademark Office*